United States Patent [19]

Berglund

[11] Patent Number: 5,808,048
[45] Date of Patent: *Sep. 15, 1998

[54] PROCESS FOR PREPARING 1-(2'-DEOXY-2', 2'-DIFLUORO-D-RIBOFURANOSYL)-4-AMINOPYRIMIDIN-2-ONE) HYDROCHLORIDE

[75] Inventor: Richard A. Berglund, Lafayette, Ind.

[73] Assignee: Eli Lilly and Company, Indianapolis, Ind.

[ * ] Notice: The term of this patent shall not extend beyond the expiration date of Pat. No. 5,637,688.

[21] Appl. No.: 837,071

[22] Filed: Apr. 11, 1997

Related U.S. Application Data

[63] Continuation of Ser. No. 355,372, Dec. 13, 1994, Pat. No. 5,637,688.

[51] Int. Cl.$^6$ .................................................. C07H 19/073
[52] U.S. Cl. .................... 536/28.5; 536/28.2; 536/28.52; 536/28.53
[58] Field of Search ................. 536/28.5, 28.2, 536/28.52, 28.53

[56] References Cited

U.S. PATENT DOCUMENTS

| | | |
|---|---|---|
| 3,817,978 | 6/1974 | Jenkins et al. . |
| 4,472,386 | 9/1984 | Kodama et al. . |
| 4,526,988 | 7/1985 | Hertel . |
| 4,808,614 | 2/1989 | Hertel . |
| 4,965,374 | 10/1990 | Chou et al. . |
| 5,223,608 | 6/1993 | Chou et al. . |
| 5,637,688 | 6/1997 | Berglund .............................. 536/28.5 |

FOREIGN PATENT DOCUMENTS

| | | |
|---|---|---|
| 184365 | 6/1986 | European Pat. Off. . |
| 576227 | 12/1993 | European Pat. Off. . |
| 577303 | 1/1994 | European Pat. Off. . |
| 577304 | 1/1994 | European Pat. Off. . |
| 587364 | 3/1994 | European Pat. Off. . |

*Primary Examiner*—James O. Wilson
*Attorney, Agent, or Firm*—Brian P. Barrett; David E. Boone

[57] ABSTRACT

This invention provides a process for preparing gemcitabine hydrochloride which comprises deblocking β-1-(2'-deoxy-2',2'-difluoro-3',5'-di-O-benzoyl-D-ribofuranosyl)-4-aminopyrimidin-2-one with a catalytic amount of an alkylamine in the presence of methanol or ethanol in an environment essentially free of water; treating the resulting solution with hydrochloric acid and an antisolvent; and recovering the resulting solid gemcitabine hydrochloride.

8 Claims, No Drawings

PROCESS FOR PREPARING 1-(2'-DEOXY-2', 2'-DIFLUORO-D-RIBOFURANOSYL)-4-AMINOPYRIMIDIN-2-ONE) HYDROCHLORIDE

This application is a continuation of application Ser. No. 08/355,372 filed Dec. 13, 1994, now U.S. Pat. No. 5,637,688.

BACKGROUND 1-(2'-Deoxy-2',2'-difluoro-D-ribofuranosyl)-4-aminopyrimidin-2-one hydrochloride (also known as 2'-deoxy -2',2'-difluorocytidine hydrochloride or gemcitabine hydrochloride—see Formula I) is one of a series of 2'-deoxy-2',2'-difluoronucleosides known in the art. For example, such compounds are disclosed and taught to have antiviral activity in U.S. Pat. Nos. 4,526,988 and 4,808,614. European Patent Application Publication 184,365 teaches that these same difluoronucleoside agents have oncolytic activity. In fact, gemcitabine hydrochloride is undergoing clinical evaluation to determine its usefulness as a treatment for a variety of cancers, such as pancreatic cancer.

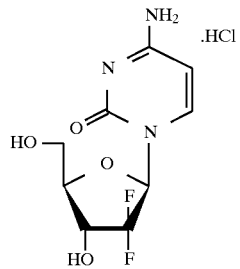

The synthesis of gemcitabine is a multi-step process—see U.S. Pat. Nos. 4,526,988, 4,808,614, and 5,223,608 and European Patent Application Publications 577,303, 577,304, and 587,364. Most of these synthetic routes go through the penultimate intermediate β-1-(2'-deoxy-2',2'-difluoro-3',5'-di-O-benzoyl-D-ribofuranosyl)-4-aminopyrimidin-2-one which is deprotected and salified to give the final desired product as the hydrochloride salt. For example, in U.S. Pat. No. 5,223,608, at column 10, line 41 et seq., it is taught that the benzoyl protecting groups "are removed by hydrolysis with a strong or moderately strong base". It is also taught that "[a]t least one mole equivalent of base is needed for each protecting group." Examples 7 and 11 of this patent teach the use of anhydrous ammonia in methanol for accomplishing this deprotection which results in the formation of ammonium chloride which is insoluble in the organic solvents used and must be removed by treatment with water.

The preparation of gemcitabine hydrochloride salt is also disclosed in the literature. U.S. Pat. No. 5,223,608, at column 11, line 22 et seq., and Example 8 where hot isopropanol and concentrated hydrochloric acid are used to generate the crystalline gemcitabine hydrochloride.

This invention provides a more economical and higher yielding process for preparing gemcitabine hydrochloride which avoids the use of excess base and loss of product due to the presence of water.

SUMMARY OF THE INVENTION

This invention provides a process for preparing gemcitabine hydrochloride which comprises:

a) deblocking β-1-(2'-deoxy-2',2'-difluoro -3',5'-di-O-benzoyl-D-ribofuranosyl)-4-aminopyrimidin-2-one with a catalytic amount of an alkylamine in the presence of methanol or ethanol in an environment essentially free of water;

b) treating the resulting solution with hydrochloric acid and an antisolvent; and c) recovering the resulting solid gemcitabine hydrochloride.

DETAILED DESCRIPTION AND PREFERRED EMBODIMENTS

I have discovered that, during the deprotection of β-1-(2'-deoxy-2',2'-difluoro-3',5'-di-O-benzoyl-D-ribofuranosyl)-4-aminopyrimidin-2-one, the protic solvent employed is the actual nucleophile which attacks the benzoyl group. This attack is catalyzed by base and stoichiometric amounts of base are not required.

When used in this application, the term "alkylamine" means an organic amine having one, two or three alkyl groups and which is capable of adjusting the pH of the reaction mixture to at least 9.5. Examples of such reagents include, methylamine, ethylamine, propylamine, isopropylamine, butylamine, dimethylamine, diethylamine, dipropylamine, diisopropylamine, dibutylamine, ethanolamine, trimethylamine, triethylamine, tripropylamine, N-methyl-N-ethylamine, N-methyl-N-propylamine, N-methyl-N-butylamine, N-ethyl-N-propylamine, and the like. As discussed below, this invention requires that the alkylamine hydrochloride must also be soluble in the reaction mixture. Further, for effective reaction conditions, the alkylamine should be sufficiently non-volatile to allow for effective reaction at elevated temperatures. For all of these reasons, I have discovered that diethylamine is the preferred alkylamine in this reaction, although other alkylamines are operable.

The term "catalytic amount" refers to an amount of alkylamine which will promote the nucleophilic attack on the benzoyl protecting groups by the protic solvent. Typically about 0.1–0.5 molar equivalents (relative to the β-1-(2'-deoxy-2',2'-difluoro-3',5'-di-O-benzoyl-D-ribofuranosyl)-4-aminopyrimidin-2-one employed) are used, most preferably from about 0.2–0.4 equivalents—however, as will be appreciated by those skilled in the art, the optimal amount of alkylamine employed will depend upon the chemical and physical properties of the alkylamine so long as the pH of the reaction mixture is maintained at no less than 9.5.

The phrase "in an environment essentially free of water" indicates that the reaction is carried out without any added water. It is therefore preferred that the reagents and solvents used be essentially free of water. The reaction mixture can be protected from atmospheric moisture but this precaution is not necessary. This limitation, which is not critical to the deblocking reaction, is preferred because the final desired gemcitabine hydrochloride is soluble in water and therefore the presence of water will reduce isolated yield of the desired product from the crystallization process.

As noted above, I have discovered that the deblocking of the β-1-(2'-deoxy-2',2'-difluoro-3',5'-di-O -benzoyl-D-ribofuranosyl)-4-aminopyrimidin-2-one is one where it protic nucleophile is catalyzed by base and that therefore it is the protic reagent that is critical to the reaction. While any protic solvent can theoretically be employed for the solvolysis to occur, it is preferred that an alcohol, preferably ethanol and most preferably methanol, be employed. This choice is preferred for several reasons—first, the substrate and alkylamine hydrochloride are soluble in methanol, as is the resulting product. Second, the resulting by-product is methyl benzoate which is also soluble in methanol and in the precipitating solvent isopropanol or acetone. The use of methanol also allows for its use both as a reagent and as a solvent. Finally, as noted above, the reagent should be essentially free of water As those familiar with this chemistry will appreciate, in theory substrates other than β-1-(2'-deoxy-2',2'-difluoro-3', 5'-di-O-benzoyl-D-ribofuranosyl)-4-aminopyrimidin-2-one can be employed—however, the protecting groups must afford a substrate and by-product which are soluble as described above. Moreover, the two protective groups do not have to be the same. Thus, substrates wherein the 3'- and/or 5'-hydroxy groups are protected with other blocking groups, such as substituted benzoyl (e.g., 4-methylbenzoyl) will be operable, if a judicious choice of alkylamine and protic solvent are employed—however, they offer no advantages and are, in fact, more expensive to use.

The solvolysis is best carried out at temperatures from about 0°–80° C.; elevated temperatures are preferred. The reflux temperature of the reaction mixture (about 50°–60° C. when methanol and diethylamine are employed) is most preferred; under these conditions, the solvolysis is generally complete in about 1–8 hours.

It is preferred that the amount of methanol or ethanol used be approximately 15–25 volumes relative to the β-1-(2'-deoxy-2',2'-difluoro-3',5'-di-O-benzoyl-D-ribofuranosyl)-4-aminopyrimidin-2-one starting material (mL/g). I have discovered that the optimal ratio is about 20 volumes of methanol. It is also preferred that the amount of antisolvent be approximately equal to the amount of methanol or ethanol used, although other ratios are operable. If the β-1-(2'-deoxy-2',2'-difluoro-3',5'-di-O -benzoyl-D-ribofuranosyl)-4-aminopyrimidin-2-one is generated in situ from 2-deoxy-2,2-difluoro-3,5-dibenzoyl-D-ribofuranosyl-1-methanesulfonate and cytosine (e.g., as described in EPO Patent Application Publication No. 577,303), the yield of β-1-(2'-deoxy-2',2'-difluoro-3',5'-di-O-benzoyl-D-ribofuranosyl)-4-aminopyrimidin-2-one is usually approximately 70%—if this reaction scheme is incorporated into the present process, the amount of methanol or ethanol used should be approximately 10–20 volumes relative to the mesylate starting material—see, e.g., Example 3 infra.

The formation and isolation of gemcitabine hydrochloride is usually carried out by cooling the solvolysis reaction mixture to ambient temperature and adding an anti-solvent such as acetone, acetonitrile, tetrahydrofuran, propanol, butanol, isobutanol, sec-butanol, or preferably isopropanol. Gemcitabine base, the alkylamine, the alkylamine hydrochloride, and methyl benzoate are all soluble in this mixture; however, upon introduction of hydrogen chloride, the desired gemcitabine hydrochloride will crystallize out while the by-products and unreacted reagents will remain in solution. The hydrogen chloride is generally added as gaseous hydrogen chloride or concentrated hydrochloric acid to a pH of about 1.5 to 2.0; excess acid, particularly hydrochloric acid, is unnecessary and may adversely affect yield. Although concentrated hydrochloric acid contains water, this minimal amount of water will not materially affect the yield.

The resulting gemcitabine hydrochloride is then isolated from the reaction mixture by conventional means, e.g., filtration, centrifugation, decantation, etc.

The starting materials and intermediates for the preparation of the compounds of the present invention are commercially available or can be readily prepared by other methods known in the literature. References to specific literature procedures are cited in the examples and listed following the example section hereinbelow.

The following examples further illustrate the preparation of the compounds of this invention. The examples are provided for purposes of illustration only and are not to be construed as limiting the scope of the instant invention in any way.

The terms and abbreviations used in the instant examples have their normal meaning unless otherwise designed, for example, "HPLC" refers to high performance liquid chromatography; "°C." refers to degrees Celsius; "mmol" refers to millimole; "g" refers to gram; "L" refers to liter; "mL" means milliliter; "M" refers to molar or molarity; "eq." means molar equivalents.

Example 1

1-(2'-deoxy-2',2'-difluoro-D-ribofuranosyl)-4-aminopyrimidin-2-one hydrochloride β-1-(2'-deoxy-2',2'-difluoro-3',5'-di-O-benzoyl-D-ribofuranosyl)-4-aminopyrimidin-2-one (0.24 g, 0.51 mmol, 1 eq.) was slurried in methanol (7 mL) then diethylamine (0.01 mL, 0.102 mmmol, 0 2 eq.) was added. The mixture was heated to 55° C. for 2 hours and 20 minutes.

To isolate the product, the mixture was filtered and the filter was rinsed with isopropanol (3.5 mL). The filtrate and rinse were combined and adjusted to a pH of 1.5 to 2.0 by adding concentrated hydrochloric acid (0.3 mL). A precipitate formed within 1 to 2 minutes. The mixture was then stirred at room temperature for 2 hours and filtered. The solid was washed with isopropyl alcohol (5 mL) then with acetone (5 mL). HPLC analysis showed the potency of the above product to be greater than 99 percent.

The identity of the major components of the solution was characterized by a HPLC comparison with authentic reference standards. The HPLC assay sample was prepared by placing 0.6–0.8 g of the reaction solution or 10 mg to 15 mg of 1-(2'-deoxy-2',2'-difluoro-D-ribofuranosyl)-4-aminopyrimidin-2-one in a 50 mL flask, then diluting to volume with water. The column was eluted with eluant: A=0.05M acetate at pH of 5.0; B=acetonitrile; flow rate at 1.5 mL/minute. Eluant profile is 97 percent A, 3 percent B hold for 5 minutes, gradient to 30 percent A, 70 percent B over 10 minutes, hold at 30 percent A, 70 percent B for 5 minutes, return to 97 percent A, 3 percent B over 2 minutes and hold for 13 minutes. The column employed was a 25 cm Zorbax RxC8 column. The detector had a wavelength of 275 nm, the column flow rate was 1.5 mL/minute and the injection volume was 10 μL.

The HPLC assay established retention times as follows: a) cytosine and other impurities, 2.4 to 2.6 minutes; b) α-1-(2'-deoxy-2',2'-difluoro-D-ribofuranosyl)-4-aminopyrimidin-2-one, 5 to 6 minutes; c) β-1-(2'-deoxy-2', 2'-difluoro-D-ribofuranosyl)-4-aminopyrimidin-2-one, 6 to 7 minutes; d) benzoic acid, 10 to 11 minutes; e) 1-(2'-deoxy-2',2'-difluoro-3' or 5'-mono-O-benzoyl-D-ribofuranosyl)-4-aminopyrimidin-2-one, 14 to 15 minutes; f) methyl benzoate; 16.5 to 17.5 minutes; and g) β-1-(2-deoxy-2',2'-difluoro-3',5'-di-O-benzoyl-D-ribofuranosyl)-4-aminopyrimidin-2-one, 19 to 20 minutes.

Example 2

1-(2'-deoxy-2',2'-difluoro-D-ribofuranosyl)-4-aminopyrimidin-2-one hydrochloride β-1-(2'-deoxy-2',2'-difluoro-3',5'-di-O-benzoyl-D-ribofuranosyl)-4-aminopyrimidin-2-one (0.24 g, 0.51 mmol, 1 eq.) was slurried in methanol (7 mL) and propylamine (0.0084 mL, 0.102 mmol, 0.2 eq.) was added. The mixture was heated to 55° C. for 3 hours.

To isolate the product, the mixture was filtered the filter was rinsed with isopropanol (3.5 mL) and the combined filtrate and rinse was adjusted to a pH of about 1.5 to 2.0 by adding concentrated hydrochloric acid (0.3 mL). A precipitate formed in 1 to 2 minutes. The mixture was then stirred at 0° C. to 50° C. for 90 minutes and filtered. The solid was washed with isopropyl alcohol (5 mL) then with acetone (5 mL). An HPLC analysis, carried out as described in Example 1, showed the potency of the isolated solid to be 98.9 percent.

Example 3

1-(2'-deoxy-2',2'-difluoro-D-ribofuranosyl)-4-aminopyrimidin-2-one hydrochloride β-1-(2'-deoxy-2',2'-difluoro-3',5'-di-O-benzoyl-D-ribofuranosyl)-4-aminopyrimidin-2-one (obtained from reaction of 3.836 g of 2-deoxy-2,2-difluoro-3,5-dibenzoyl-D-ribofuranosyl-1-methanesulfonate (8.4 mmol) and 20.0 g (180 mmol) of cytosine as described in EPO Patent Application Publication No. 577,303) was slurried in methanol (54 mL). The mixture was heated to 50° C. with stirring and adjusted to a pH of 10 by adding diethylamine (0.3 mL, 2.9 mmol, 0.34 eq.). The stirring continued and the mixture was heated to 55° C. to 60° C. for 14 hours.

To isolate the product, decolorizing charcoal (0.17 g) and isopropyl alcohol (40 mL) were added and the mixture was stirred at 20° C. to 25° C. for 1 hour. The mixture was cooled to 0° C. to 5° C., stirred for 30 minutes, then filtered through a pad of filter aid. The filter cake was washed with isopropyl alcohol (14 mL). The combined filtrate was adjusted to a pH of about 1.5 to 1.8 by adding concentrated hydrochloric acid (0.95 mL). A precipitate formed and the mixture was stirred at 0° C. to 5° C. for 2 hours then filtered. The solid was washed with isopropyl alcohol (2×15 mL) then with acetone (1×15 mL). An HPLC analysis, carried out as described in Example 1, showed the potency of the isolated solid to be 99.4 percent. The overall yield of the product was 57.6 weight percent (based on mesylate).

Example 4

1-(2'-deoxy-2',2'-difluoro-D-ribofuranosyl)-4-aminopyrimidin-2-one hydrochloride β-1-(2'-deoxy-2',2'-difluoro-3',5'-di-O-benzoyl-D-ribofuranosyl)-4-aminopyrimidin-2-one (2.58 g, 5.48 mmol) was slurried in methanol (56 mL). The mixture was heated to 40° C. to 45° C. with stirring and the pH adjusted to 10 by adding diethylamine (0.1 mL, 0.97 mmol, 0.2 eq.). The stirring continued and the mixture was heated to 50° C. to 60° C. for 6.5 hours. The mixture was then stirred at 20°–25° C. overnight (15 hours).

To isolate the product, decolorizing charcoal (0.2 g) and isopropyl alcohol (42 mL) were added and the mixture was stirred at room temperature for 1 hour. The mixture was filtered through a pad of filter aid and the filter cake was washed with isopropyl alcohol (14 mL). Methanol was added to the combined filtrate to adjust the total volume of solution to 112 mL. The solution was then divided into two equal volumes. One solution was adjusted to a pH of 1.5 and the other adjusted to a pH of 2.5 by adding concentrated hydrochloric acid. Both solutions were cooled to 0° C. to 5° C., stirred for 2 hours, then filtered. The solid filter cake from each solution was washed with isopropyl alcohol (5 mL) then with acetone (5 mL). After drying, a product yield of 89.6 weight percent from the 1.5 pH solution and 82.8 weight percent from the 2.5 pH solution was obtained. An HPLC analysis, carried out as described in Example 1, showed the product potency of the material obtained at pH of 1.5 to be 99.1%; the potency of the material obtained at pH 2.5 was 99.6%.

Example 5

1-(2'-deoxy-2',2'-difluoro-D-ribofuranosyl)-4-aminopyrimidin-2-one hydrochloride β-1-(2'-deoxy-2',2'-difluoro-3',5'-di-O-benzoyl-D-ribofuranosyl)-4-aminopyrimidin-2-one (0.24 g, 0.51 mmol) was slurried in methanol (7 mL) containing 0.03 mL diethylamine (0.26 mmol, 0.5 equiv.). The mixture was heated to 50° C. to 60° C. with stirring for 6 hours.

To isolate the product, the mixture was cooled to room temperature and isopropyl alcohol (7 mL) was added. The pH of the mixture was adjusted to pH 1.5 by adding concentrated hydrochloric acid (0.30 mL). After stirring for 2–3 minutes, a precipitate formed. The stirring continued for 1 hour at 0° C. to 50° C.; the mixture was then filtered. The yield of the product (0.15 g) formed was 98 weight percent.

I claim:

1. A process for preparing gemcitabine which comprises: deblocking β-1-(2'-deoxy-2',2'-difluoro-3',5'-di-O-benzoyl-D-ribofuranosyl)-4-aminopyrimidin-2-one with a catalytic amount of an alkylamine in the presence of methanol or ethanol in an environment essentially free of water.

2. A process for preparing gemcitabine which comprises:
   a) deblocking β-1-(2'-deoxy-2',2'-difluoro-3',5'-di-O-benzoyl-D-ribofuranosyl)-4-aminopyrimidin-2-one with a catalytic amount of an alkylamine in the presence of methanol or ethanol in an environment essentially free of water; and
   b) recovering the resulting gemcitabine.

3. The process of claim 1 wherein the alkylamine is diethylamine.

4. The process of claim 1 wherein the deblocking is conducted in the presence of methanol.

5. The process of claim 4 wherein approximately 15–25 mL of methanol is used per gram of β-1-(2'-deoxy-2',2'-difluoro-3',5'-di-O-benzoyl-D-ribofuranosyl)-4-aminopyrimidin -2-one.

6. The process of claim 5 wherein approximately 20 mL of methanol is used per gram of β1-(2'-deoxy-2',2'-difluoro-3',5'-di-O-benzoyl-D-ribofuranosyl)-4-aminopyrimidin-2-one.

7. The process of claim 1 wherein the β-1-(2'-deoxy-2',2'-difluoro-3',5'-di-O-benzoyl-D-ribofuranosyl)-4-aminopyrimidin-2-one is generated in situ from 2-deoxy-2,2-difluoro-3,5-dibenzoyl-D-ribofuranosyl-1-methanesulfonate and cytosine.

8. The process of claim 7 wherein approximately 10–20 mL of methanol is used per gram of 2-deoxy-2,2-difluoro-3,5-dibenzoyl-D-ribofuranosyl-1-methanesulfonate.

* * * * *